US012661083B2

(12) United States Patent
Maule et al.

(10) Patent No.: US 12,661,083 B2
(45) Date of Patent: Jun. 23, 2026

(54) SYSTEMS AND METHODS FOR A CALIBRATION PHANTOM HOLDER

(71) Applicant: GE Precision Healthcare LLC, Waukesha, WI (US)

(72) Inventors: Sam Maule, Hartford, WI (US); Mason Dieck, Waukesha, WI (US); Michelle Marie Severino DeLong Samalik, Franklin, WI (US); Chelsey Amanda Lewis, Waukesha, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 149 days.

(21) Appl. No.: 18/789,440

(22) Filed: Jul. 30, 2024

(65) Prior Publication Data

US 2026/0033798 A1 Feb. 5, 2026

(51) Int. Cl.
| | |
|---|---|
| *A61B 6/58* | (2024.01) |
| *A61B 6/04* | (2006.01) |
| *A61B 6/42* | (2024.01) |

(52) U.S. Cl.
CPC ............ *A61B 6/583* (2013.01); *A61B 6/0407* (2013.01); *A61B 6/4241* (2013.01)

(58) Field of Classification Search
CPC ..... A61B 6/583; A61B 6/0407; A61B 6/4241; A61B 6/032; A61B 6/4411
See application file for complete search history.

(56) References Cited

U.S. PATENT DOCUMENTS

| | | |
|---|---|---|
| 2005/0259793 A1 | 11/2005 | Yeo et al. |
| 2025/0359832 A1* | 11/2025 | Maule ..................... A61B 6/04 |

OTHER PUBLICATIONS

Maule, S. et al., "Methods and Systems for a Cradle Clamping Holder," U.S. Appl. No. 18/670,577, filed May 21, 2024, 50 pages.

* cited by examiner

*Primary Examiner* — Courtney D Thomas
(74) *Attorney, Agent, or Firm* — McCoy Russell LLP

(57) ABSTRACT

A calibration phantom holder for an imaging system is provided. In one example, the calibration phantom holder includes a horizontal member with a plurality of parallel slots distributed along an upper surface of the horizontal member. Each parallel slot of the plurality of parallel slots is configured to support one or more calibration phantoms. The calibration phantom holder includes a vertical member perpendicularly coupled to the horizontal member. The vertical member configured to couple to a support system of the imaging system.

20 Claims, 16 Drawing Sheets

1200

START

1202
MOUNT THE CALIBRATION PHANTOM HOLDER TO A
SUPPORT SYSTEM OF THE IMAGING SYSTEM

1204
PREPARE ONE OR MORE CALIBRATION PHANTOMS

1206
SLOT ONE OR MORE SLOTTED SLABS INTO THE
CALIBRATION PHANTOM HOLDER

1208
POSITION CALIBRATION PHANTOM HOLDER INTO A
BORE OF THE IMAGING SYSTEM

1210
PERFORM CALIBRATION ACCORDING TO FIG. 13

END

SYSTEMS AND METHODS FOR A CALIBRATION PHANTOM HOLDER

TECHNICAL FIELD

Embodiments of the subject matter disclosed herein relate to a phantom and more particularly, to a holder for one or more phantoms used to calibrate a photon counting CT scanner.

BACKGROUND

In computed tomography (CT) imaging systems, an electron beam generated by a cathode is directed towards a target within an X-ray source or X-ray tube. A fan-shaped or cone-shaped beam of X-rays produced by electrons colliding with the target is directed towards a subject, such as a patient. After being attenuated by the object, the X-rays impinge upon an array of X-ray detectors, generating an image. One example of a CT system is a Photon Counting CT (PCCT) system, where the X-ray detectors are photon-counting detectors, and photons are counted to provide spectral information. A calibration process may be performed periodically on the PCCT system. The calibration process may include performing a CT imaging procedure on an object, called a phantom, and generating a correction factor based on the resulting image of the phantom. The phantom may be made of stacked slabs of material and the content of the layers may be changed between calibration scans. In some examples, the calibration process may include scanning multiple stacks, and adding or removing slabs from a stack between calibration scans. Additionally, the stacked slabs are positioned in the path of an X-ray beam during a scan to perform a calibration.

BRIEF DESCRIPTION

In one example, a calibration phantom holder for an imaging system is provided. The calibration phantom holder includes a horizontal member comprising a plurality of parallel slots distributed along an upper surface of the horizontal member, each parallel slot of the plurality of parallel slots configured to support one or more calibration phantoms. The calibration phantom holder includes a vertical member perpendicularly coupled to the horizontal member, the vertical member configured to couple to a support system of the imaging system.

The above advantages and other advantages and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
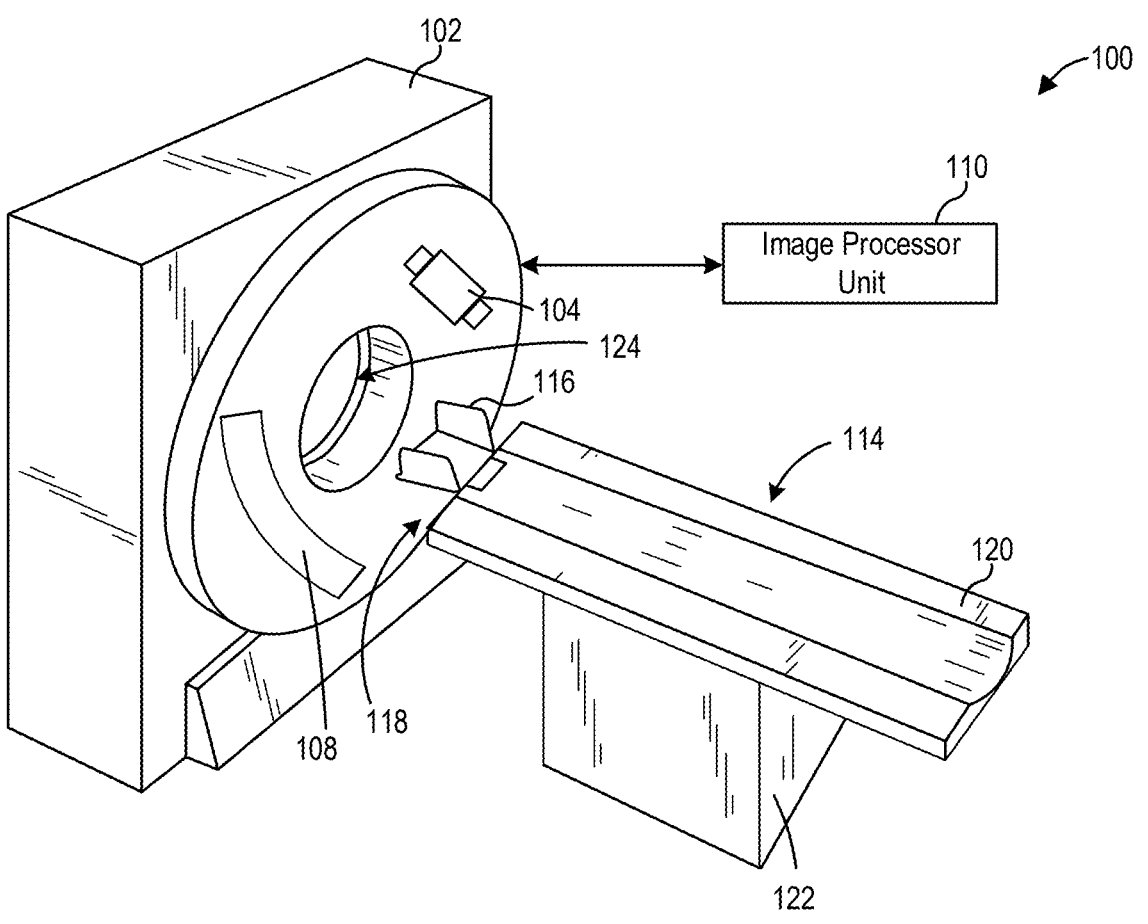
FIG. 1 shows a pictorial view of a photon counting computed tomography (PCCT) imaging system, in accordance with one or more embodiments of the present disclosure.

The description and embodiments of the subject matter disclosed herein relate to a phantom holder for calibration scans of an imaging system, such as a photon counting computed tomography (PCCT) system. Imaging systems, such as PCCT systems, may demand regular calibration scans, such as daily or weekly calibration scans to offset any gain drift, realized from hardware such as X-ray tube focal spot position change, or radiation degradation of the detectors. Further, PCCT systems may obtain spectral information that allows generation of basis material decomposition (BMD) images. Calibrating PCCT systems may thereby demand that calibration projection data be obtained that mimics the materials and material thicknesses of the human body. Thus, phantoms for calibrating PCCT systems may include multiple different materials, such as slabs of poly-vinyl chloride (PVC) and polyethylene (PE) arranged in stacks. In some examples, more than one stack may be scanned during the calibration process. Additionally, slabs may be added or removed to a stack during a calibration process.

In current approaches, stacks of slabs are scanned one-at-a-time, the stacks top-loaded manually onto a holder, or directly onto a cradle, and into the scanning path of the PCCT system by a technician. The slabs are often large and heavy, and there is limited space for loading and changing stacks of slabs, resulting in a source of potential injury to technicians and damage to the slabs. Thus, for calibration processes that may include as many as forty combinations of slabs, calibrating PCCT systems may be physically demand-ing and time-consuming. Further, current approaches are prone to misalignment, which may negatively impact cali-brations.

Thus, a calibration phantom holder is disclosed herein which reduces the quantity and the footprint of components required for calibration while also reducing the number of user interactions of the technician doing the calibration. The calibration phantom holder includes a horizontal member and a vertical member perpendicularly coupled to the hori-zontal member. The horizontal member includes a plurality of parallel slots distributed along an upper surface of the horizontal member. Each parallel slot of the plurality of parallel slots is configured to support one or more calibration phantoms. The vertical member is configured to couple to a support system, which may allow the phantom holder to be coupled to a cradle (e.g., of a patient table) of the PCCT scanner and positioned into the scanning path. In this way, the phantom holder accommodates easy loading of inter-changeable phantoms, where phantoms may be added or subtracted to the phantom holder during the calibration process.

The disclosed calibration phantom holder is designed to support modular slab phantoms, where several combinations of slabs may be stacked next to each other. The horizontal member has an open platter design, which is configured to support a plurality of slabs stacked vertically one on top of another, arranged horizontally side by side, or both. Rather than loading from the top, the slots of disclosed calibration phantom holder enable side-loading of slabs. Each slot of the plurality of parallel slots may include a dovetailed shape, and in some examples, may include one or more detents. The calibration phantoms supported by the holder may comprise slotted slabs, which may be slid into the corresponding slots of the phantom holder from either side of the horizontal member, reducing user effort to load the slabs. Another advantage of side loading is increased maneuverability in the typically spatially-constrained vicinity of the CT scan-ner. Further, the vertical member may include one or more apertures configured to act as handles. In this way, the calibration phantom holder may be easily transported from storage to the CT scanner.

To simplify user interactions, the entire holder loaded with multiple stacks of slabs may be adjusted into the bore of the PCCT system for scanning. The stacks may be scanned in a sequential order that reduces interactions to removing a slab from the top of the stack or adding a slab to the top. In some embodiments of the slab holder it may be possible to remove slabs from the bottom of the stack as well as the top of the stack. In some examples, the calibra-tion phantoms, e.g., the slotted slabs, may include an upper slot and lower tab. The lower tab may be configured to slide into a corresponding slot of the plurality of slots, and the upper slot may be configured to support a second calibration phantom. Thus, slotted slabs of various densities, dimen-sions, materials, etc., may be stacked in various combina-tions, which are easily added or removed from the holder.

Another advantage of the slotted design may include reduced incidence of misalignment, as the slots may act as guides for reproducible positioning of the calibration phan-toms. Further, in some examples, the slotted slabs may include an aperture configured to receive a rod that may be inserted vertically through a stack, and where in some examples, the rod may be coupled to the horizontal member. The rods and rod-apertures may act as additional guides for reproducible positioning of the calibration phantoms. Addi-tionally, or alternatively, detents may be used to maintain the position of the calibration phantoms. Further, the calibration phantom holder may be constructed out of one of the base materials used in the calibration process, such as, for example, nonmetallic material. In this way, the calibration phantom holder itself may act as a base material for all the slab combinations stacked on it, allowing it to be scanned through. By enabling scanning multiple combinations of slabs at once, and reducing the number of slabs needed for calibration, the disclosed calibration phantom holder, and the systems and methods for the disclosed calibration holder, increases efficiency in the calibration process.

Figure 2:
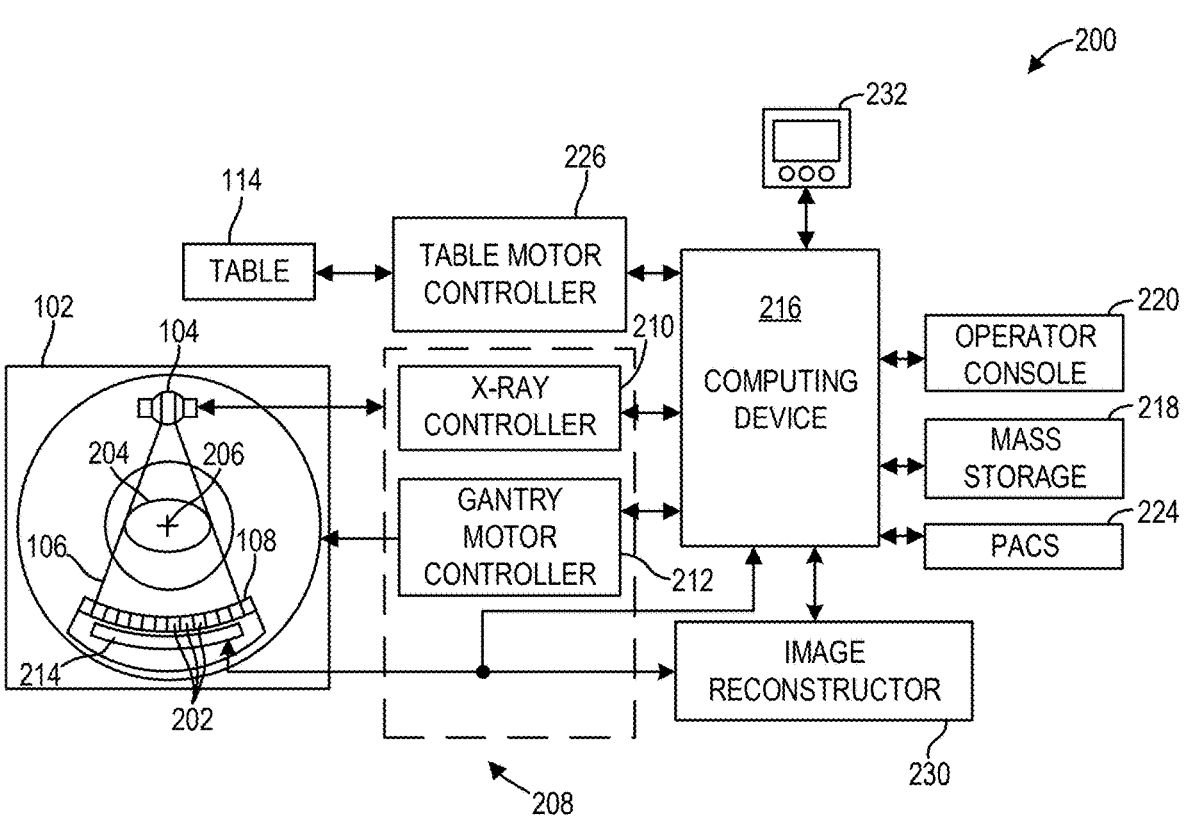
FIG. 2 shows a block schematic diagram of an example PCCT imaging system, in accordance with one or more embodiments of the present disclosure.
Figure 8:
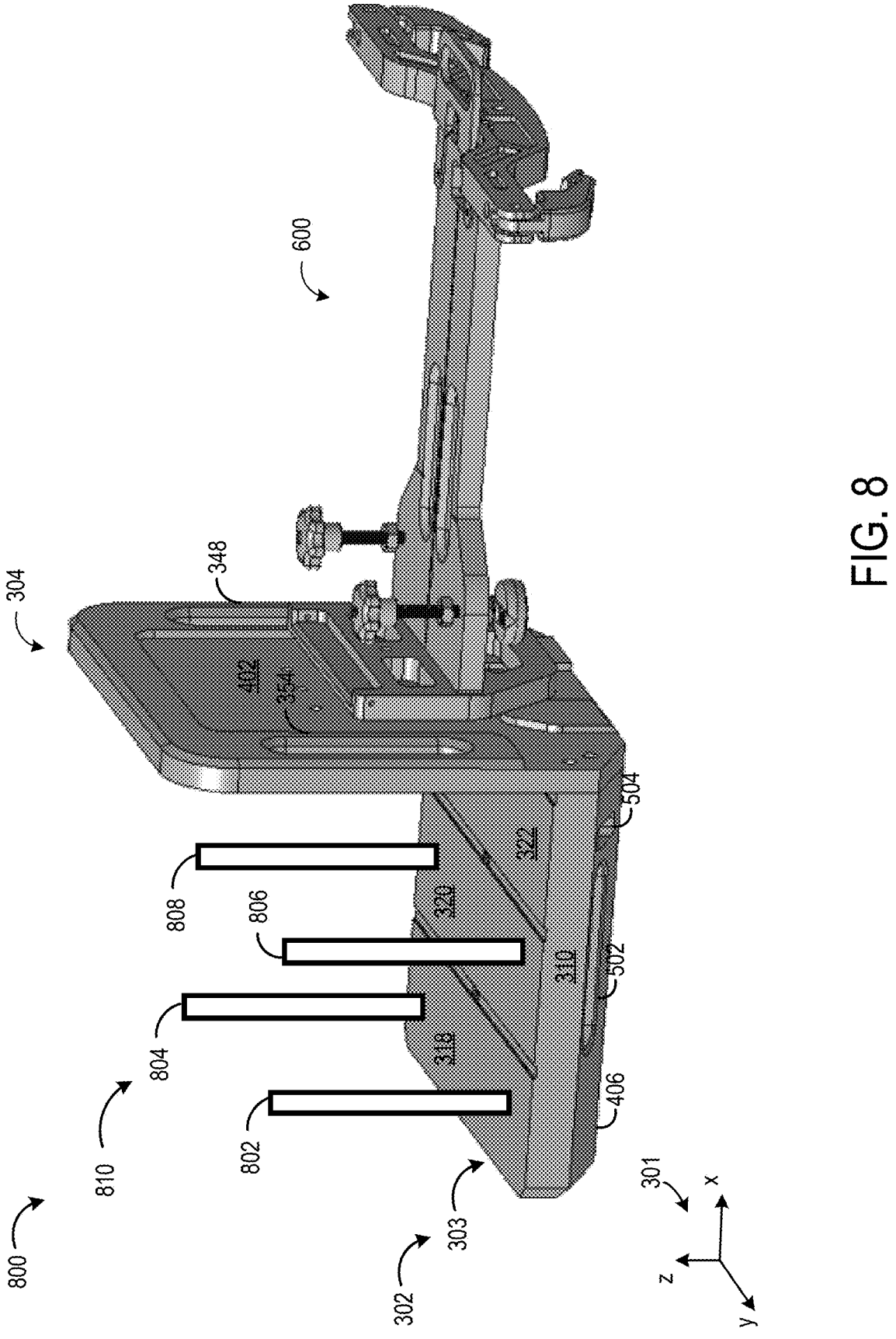
FIG. 8 shows a rear perspective view of third example of a calibration phantom holder coupled to a cradle clamp holder and including one or more rods to fix slabs in place, according to embodiments of the present disclosure.
Figure 9:
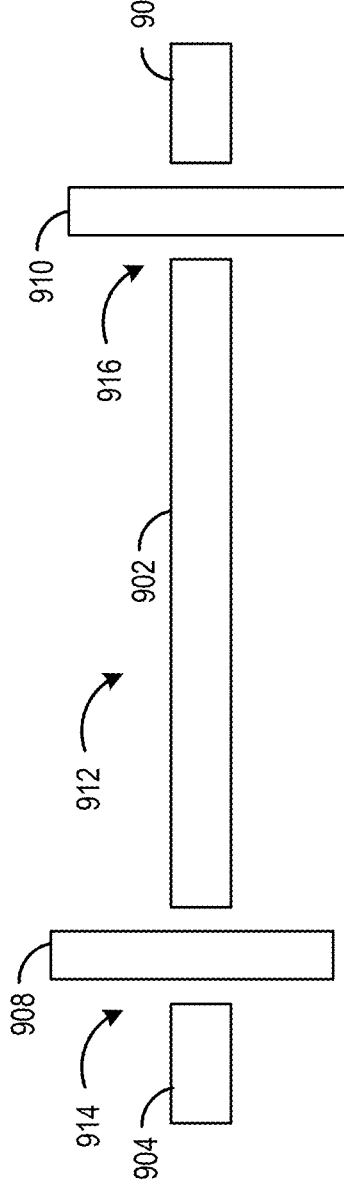
FIG. 9 is a schematic view of a slab coupled to a rod such as one of the rods shown in FIG. 8, according to embodiments of the present disclosure.
Figure 9:
Figure 12:
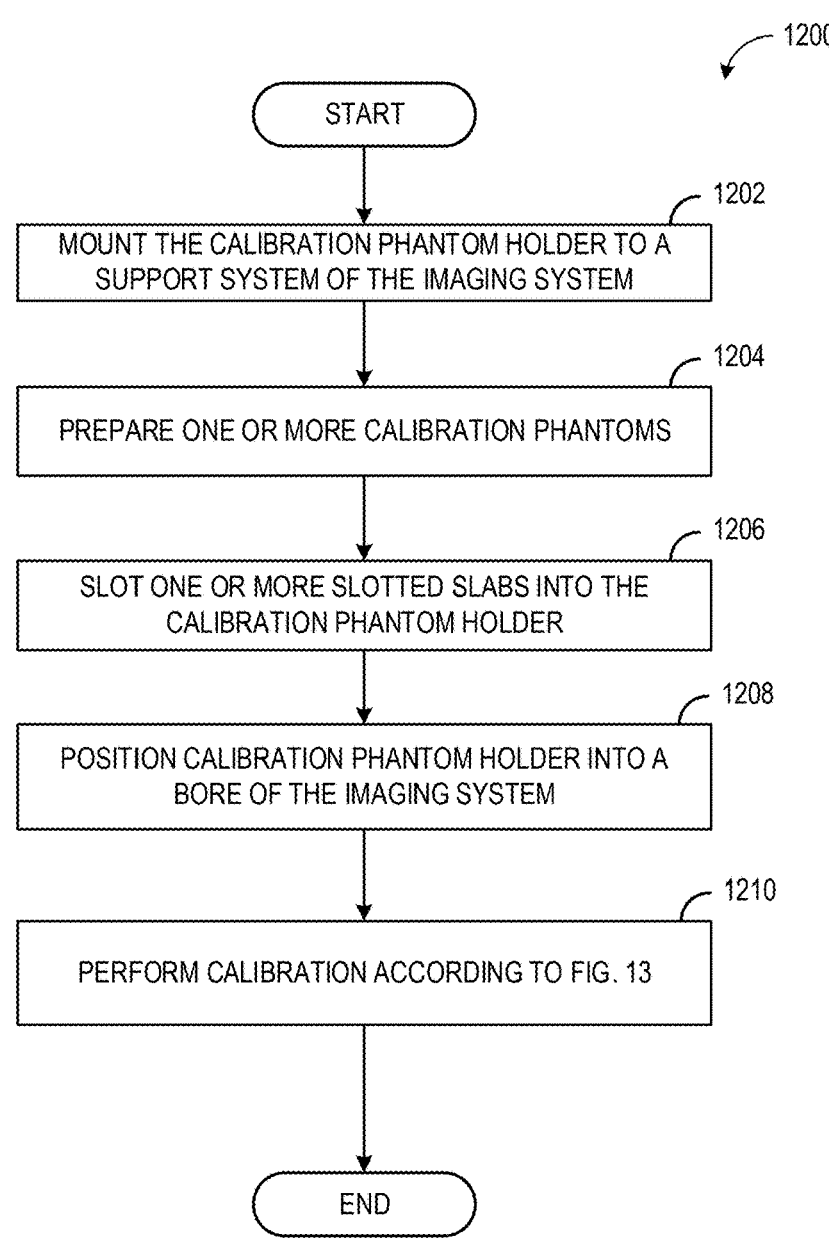
FIG. 12 is a flowchart illustrating a method for preparing calibration phantom holder to be used in a calibration, according to embodiments of the present disclosure.
Figure 13:
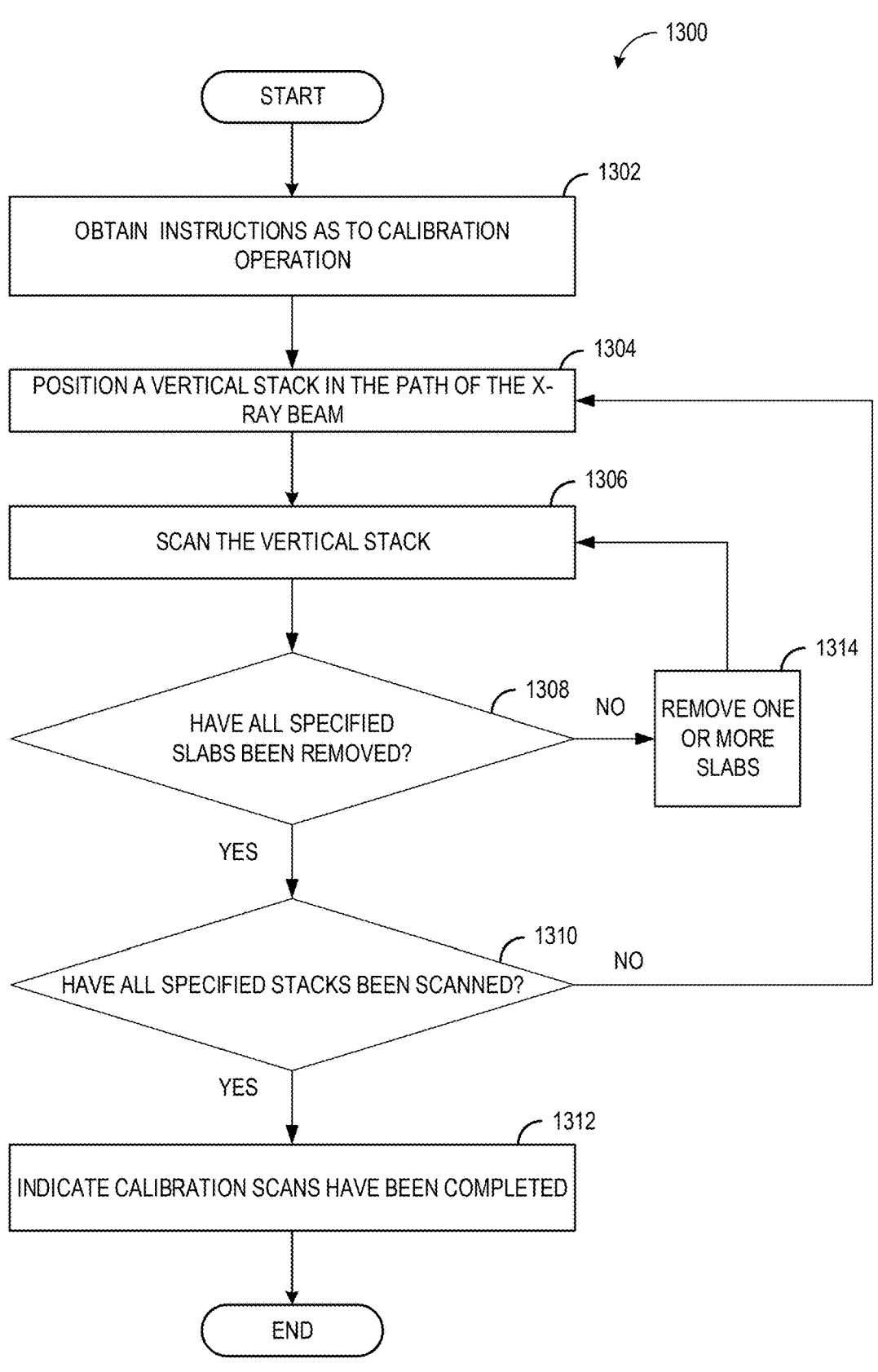
FIG. 13 is a flowchart illustrating a method for calibrating a PCCT machine using a phantom assembled on a calibration phantom holder, according to embodiments of the present disclosure.
Figure 14:
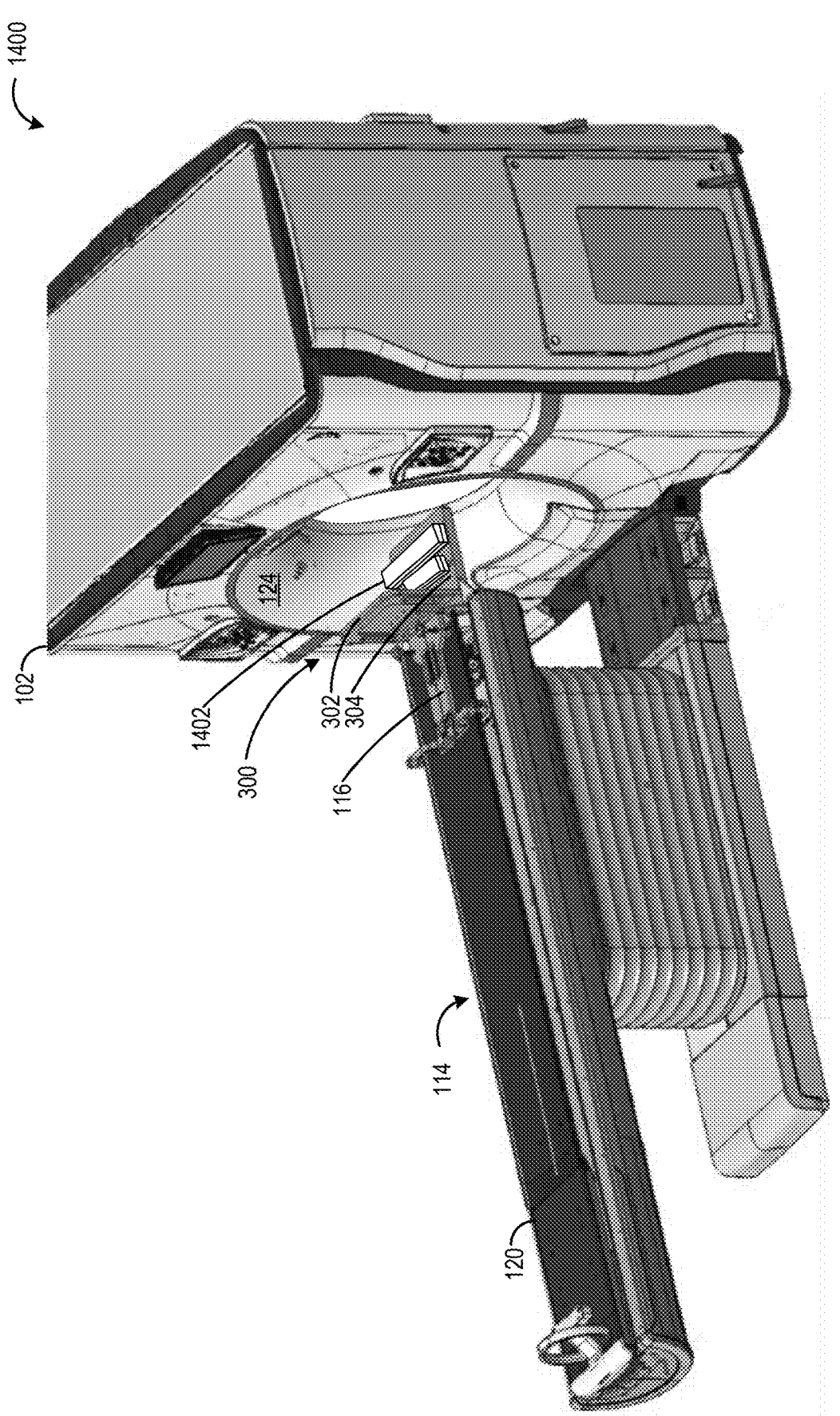
FIG. 14 is a perspective view of an example calibration phantom holder positioned for a calibration operation in an imaging system, according to embodiments of the present disclosure.

The calibration phantom holder may be used with a PCCT system, such as the PCCT system described with respect to FIGS. 1 and 2. An example calibration phantom holder that may hold one or more slabs to form a phantom is shown in FIGS. 3-6. As discussed above, the holder may have a flat base and a vertical back panel coupled to the flat base at a right angle. An example slab is shown mated to the flat base of a second example of a calibration phantom holder in FIG. 7. Examples of slabs with apertures, which may be fixed to the holder by rods inserted through the apertures, are shown in FIGS. 8-9. The slabs may be stacked in a particular order based on the clinical goals of the PCCT scanner, and slabs may be added to the stack or removed from the stack between scans during the calibration process. Example slab configurations may be seen in FIGS. 10-11. The vertical back panel of the holder may include an attachment site for a support system, such as a cradle clamping holder, which may allow the phantom holder to be coupled to the cradle of the PCCT system. An example of a calibration phantom holder coupled to a cradle clamping holder is shown in FIG. 6. FIGS. 12-13 illustrate methods for using an example of the disclosed phantom holder for calibrating a PCCT machine. An example of the disclosed phantom holder positioned for a calibration scan in an example PCCT machine is shown in FIG. 14. Example detents may be viewed in FIG. 15.

FIG. 1 illustrates an exemplary imaging system 100 configured for CT imaging. Particularly, the imaging system 100 is configured to image a subject such as a patient, an inanimate object, one or more manufactured parts, and/or foreign objects such as dental implants, stents, and/or con-trast agents present within the body. In one embodiment, the imaging system 100 includes a gantry 102, which in turn, may further include at least one X-ray source 104 configured to project a beam of X-ray radiation 106 (see FIG. 2) for use in imaging the subject laying on and/or cantilevered off of an end of a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams 106 for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the imaging system 100 further includes an image processor unit 110 configured to reconstruct images of a target volume of the subject using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject. As described further herein, in some examples the image processor unit 110 may use both an analytic image reconstruction approach, such as FBP, in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of a radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the radiation beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

The table 114 includes a cradle 120 supported by a base 122. In some examples, the base 122 may include wheels configured to enable movement of the table 114 into and out of a bore 124 of the gantry 102. The cradle 120 includes a support system 116 configured to support an imaging subject, such as a phantom and/or a patient body. The support system 116 is coupled to a first end 118 of the cradle 120, such that the support system 116 and the imaging subject supported thereby may be inserted into the gantry 102 of the imaging system 100. As disclosed herein, the support system 116 may be configured to support a calibration phantom holder which is inserted into the bore 124 of the gantry 102 during a calibration operation. An example support system 116 may include a cradle clamping holder configured to couple to the cradle 120 of the imaging system 100 using clamps that attach to sides of the cradle 120. The cradle clamping holder is configured to support (e.g., cantilever off of the first end 118 of the cradle 120) imaging subjects that may have a greater weight than is supported by conventional examples of the support system 116, such as the disclosed calibration phantom holder supporting a plurality of slabs. Further detail of an example of the cradle clamping holder is described with respect to FIGS. 6 and 8.

FIG. 2 illustrates an exemplary imaging system 200 similar to the imaging system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Though a CT system is described by way of example, it should be understood that the present technology may also be used on other imaging modalities, such as X-ray imaging systems, magnetic resonance imaging (MRI) systems, nuclear medicine imaging systems, positron emission tomography (PET) imaging systems, single-photon emission computed tomography (SPECT) imaging systems, ultrasound imaging systems, and combinations thereof (e.g., multi-modality imaging systems, such as PET/CT or PET/MR imaging systems). The present discussion of a CT imaging modality is provided merely as an example of one suitable imaging modality.

Figure 3:
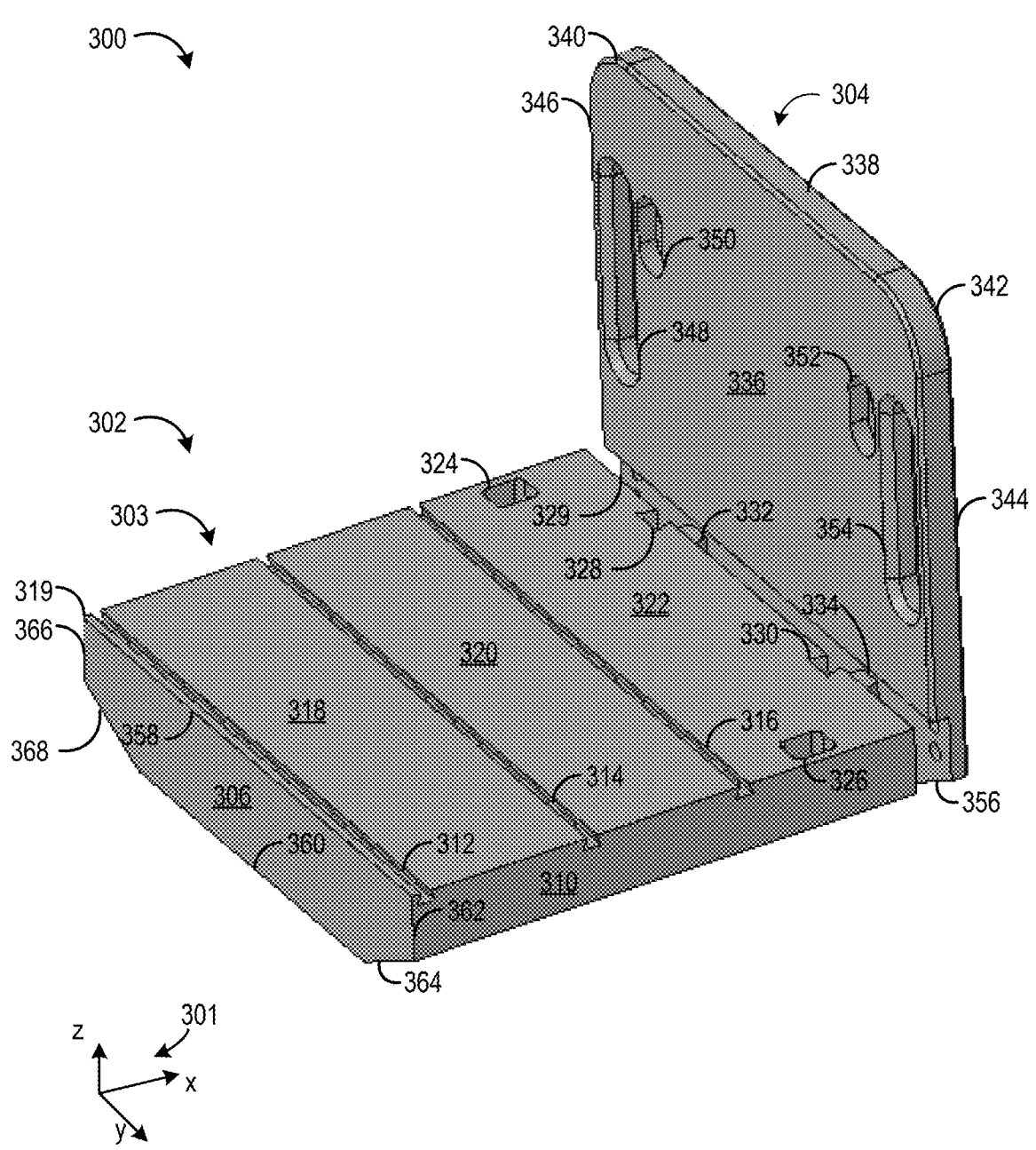
FIG. 3 shows a front perspective view of a first example of a calibration phantom holder, according to embodiments of the present disclosure.
Figure 4:
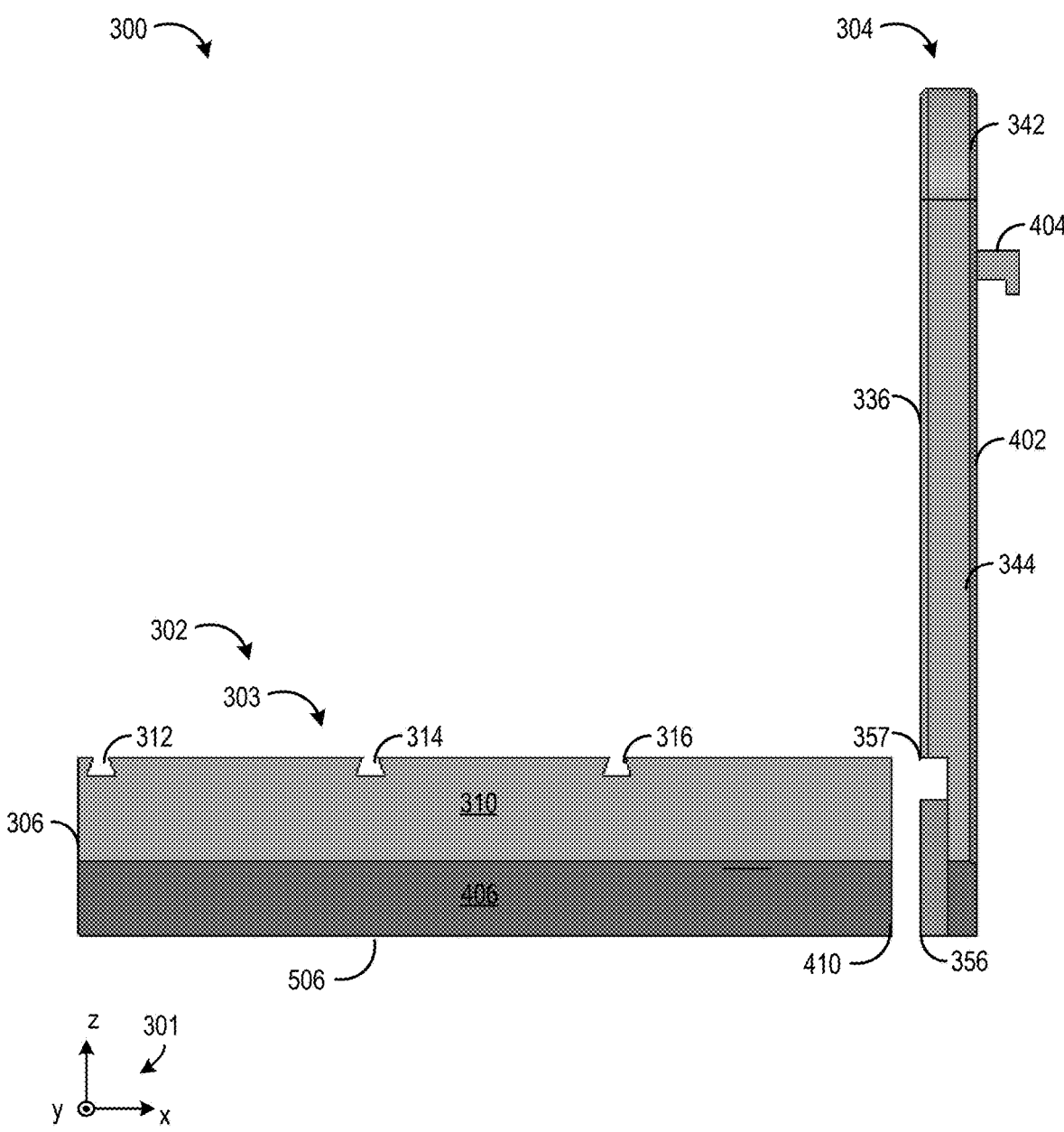
FIG. 4 shows a side view of the calibration phantom holder of FIG. 3, according to embodiments of the present disclosure.
Figure 5:
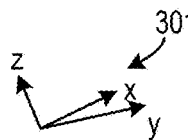
FIG. 5 shows a rear perspective view of the calibration phantom holder of FIG. 3, according to embodiments of the present disclosure.
Figure 6:
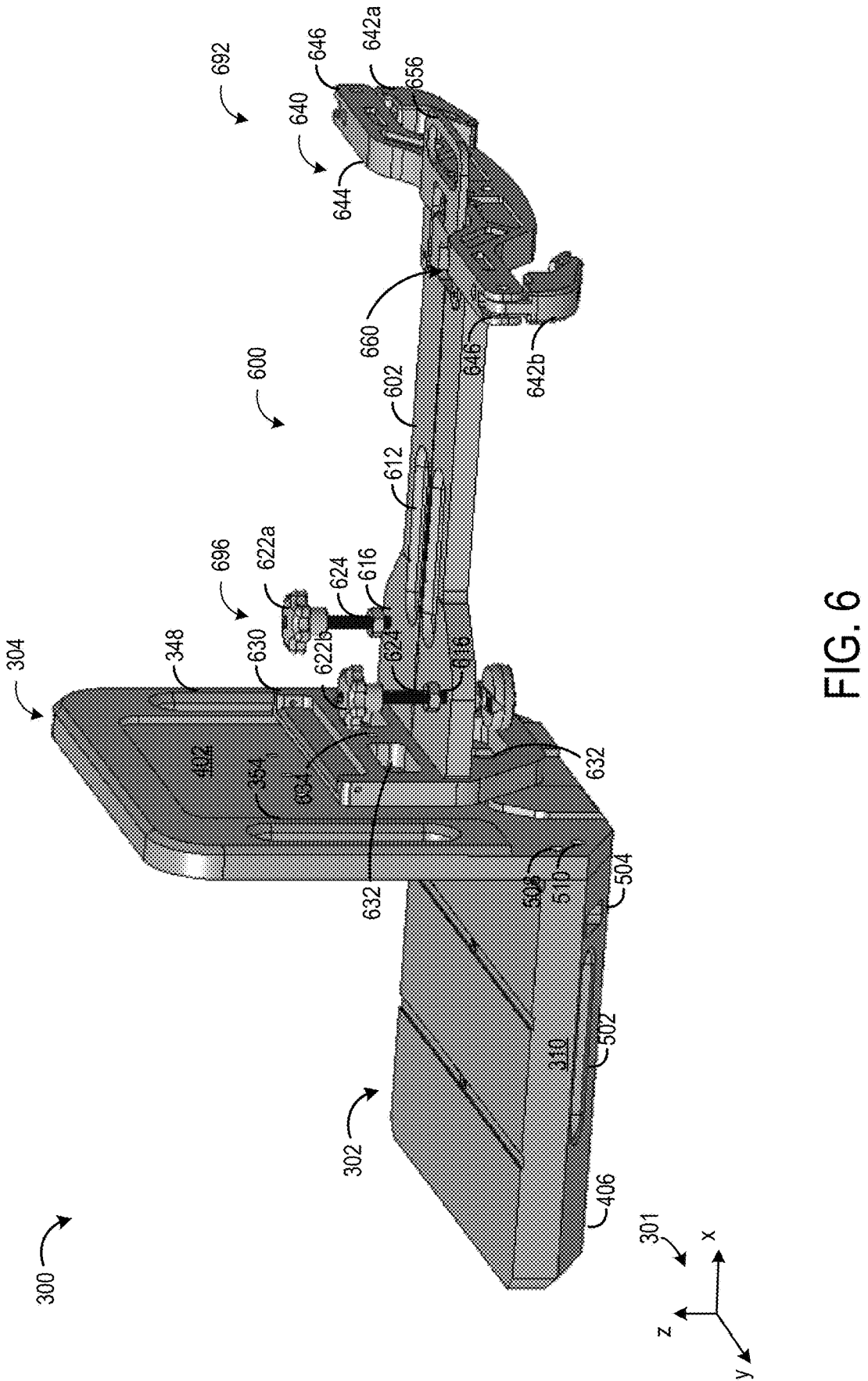
FIG. 6 shows a rear perspective view of the calibration phantom holder of FIG. 3 coupled to a cradle clamp holder, according to embodiments of the present disclosure.

FIGS. 3-5 depict a plurality of views of a calibration phantom holder 300, and are described collectively. Some elements of the calibration phantom holder 300 may be visualized in one or more of FIGS. 3-5, may be at least partially obstructed from view in one or more of FIGS. 3-5, or may be omitted from view in one or more of FIGS. 3-5. Each of FIGS. 3-5 includes a Cartesian coordinate system 301. The z-axis of coordinate system 301 may be a vertical axis (e.g., parallel to a gravitational axis), the y-axis of coordinate system 301 may be a longitudinal axis (e.g., horizontal axis), and/or the x-axis of coordinate system 301 may be a lateral axis, in one example. However, the axes may have other orientations, in other examples. When referencing direction, positive may refer to in the direction of the arrow of the x-axis, y-axis, and z-axis and negative may refer to in the opposite direction of the arrow of the x-axis, y-axis, and z-axis. A filled circle may represent an arrow and axis facing toward, or positive to, a view. An unfilled circle may represent an arrow and an axis facing away, or negative to, a view. Further, FIGS. 3-5 are drawn to scale, though other relative dimensions could be used if desired.

The calibration phantom holder 300 may be made of a material such as PVC or PE. The calibration phantom holder 300 may include a vertical member 304 and a horizontal member 302. The vertical member 304 may be a slab positioned at a right angle to the horizontal member 302. The horizontal member 302 may lie parallel to the ground when the calibration phantom holder 300 is installed in a PCCT imaging system 100.

Figure 16:
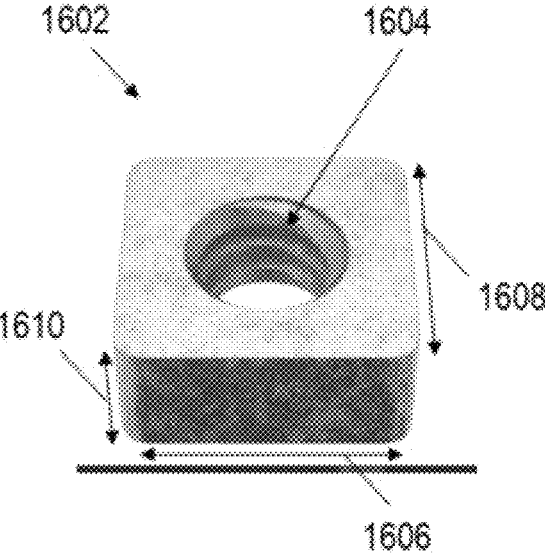
FIG. 16 is a perspective view of an example threaded insert for a calibration phantom holder according to embodiments of the present disclosure.

The horizontal member 302 may be configured to support the weight of one or more slabs that may be installed on the calibration phantom holder 300 during a calibration process. The horizontal member 302 may include a rectangular top 303, that in one example may have a length of 40-60 cm and a width of 45-70 cm. The top 303 may include a first top surface 319, a second top surface 318, a third top surface 320 and a fourth top surface 322 that lie in the x-y plane at a first position along the z axis. The top surfaces may have the same extent along the y axis as the horizontal member 302, but may vary in width along the x axis. For example, the first top surface 319 may be significantly thinner than the second top surface 318, the third top surface 320 and the fourth top surface 322. In some examples, the second top surface 318, the third top surface 320 and the fourth top surface 322 may have an equal width that may accommodate the width of a calibration phantom. The fourth top surface 322 may include a first threaded insert pocket 324 and a second threaded insert pocked 326, which may be shaped to accommodate a threaded insert. The first threaded insert pocket 324 and the second threaded insert pocket 326 may extend in the −z direction from the top surface 322 and may not extend through the entirety of the horizontal member 302 along the z axis. In other examples of the calibration phantom holder 300, the threaded insert pockets may extend from the bottom of the horizontal member 302 in the +2 direction. FIG. 16 depicts an example threaded insert 1602 which may be positioned within any of the threaded insert pockets 324, 326. The threaded insert 1602 includes a threaded portion 1604 to receive a bolt or other threaded fastener to couple, for example, the horizonal member 302 and the vertical member 304 of the calibration phantom holder 300. The example threaded insert 1602 is shaped to correspond with the shape of the threaded insert pocket 324, 326 in which the threaded insert will be positioned. That is, for a length dimension 1606, a width dimension 1608, and a depth dimension 1610 of the threaded insert correspond with a length dimension, a width dimension, and a depth dimension of the threaded insert pocket 324, 326 such that the threaded insert 1602 may be press fit into the threaded insert pocket 324, 326. In other examples, threaded insert pockets and corresponding threaded inserts may have a different shape, such as circular, hexagonal, etc.

The top 303 may further include a first slot 312, a second slot 314, and a third slot 316. The slots may be parallel to one another and lie parallel to the y-axis. The slots may extend from the top 303 in the −z direction 0.5-3 cm. In the example of the calibration phantom holder 300 the slots have a dovetailed profile, however, other configurations are possible, such as a t-slot shape. A calibration phantom may have a tab configured to mate with the slot that allows the phantom to be slid into the slot from a side such as a first side 310. In one example there may be detents within the slots that may function to stop a calibration phantom from changing position once inserted. Example detents may be viewed in FIG. 15. The slots are situated such that a calibration phantom inserted into the first slot 312 may rest on the second top surface 318, a calibration phantom inserted into the second slot 314 may rest on the third top surface 320 and a calibration phantom inserted into the third slot 316 may rest on the fourth top surface 322.

The fourth top surface 322 may include a first dovetail inlet 328 and a second dovetail inlet 330. The dovetail inlets may be three sided inlets on an edge 329 of the fourth top surface 322 closest to the vertical member 304. The dovetail inlets may extend a distance in the z-direction from the top 303 less than the height of the horizontal member 302. The first dovetail inlet 328 may include a first joint 332 and the second dovetail inlet 330 may include a second joint 334. The joints may couple the horizontal member 302 to the vertical member 304 at a right angle.

In addition to the top 303, the horizontal member 302 may include a front 306, a bottom 506, the first side 310, a second side 406, and a back 410. In one example, the front 306 may be a first front. The front 306 and the back 410 may be identical in shape and lie in x-z planes separated by the extend of the calibration phantom holder 300 along the x-axis. The shape of the front 306 is visible in FIG. 3. The front 306 may be hexagonal in shape, with a front top 358, a front bottom 360, a first front side 362, a second front side 364, a third front side 366, and a fourth front side 368. The front top 358 may be a horizontal edge parallel to the y-axis that couples the front 306 to the first top surface 319. The front bottom 360 may be a horizontal edge parallel to the y-axis that couples the front 306 to the bottom 506. The front bottom 360 may be shorter than the front top 358. The first front side 362 may be a straight edge along the z-axis that couples the front 306 to the first side 310. The first front side 362 may be coupled to the front top 358 at a right angle. The first front side 362 may be shorter than the distance between the front bottom 360 and the front top 358. The second front side 364 may couple the front 306 to the second side 406. Additionally, the second front side 364 may be coupled to the first front side 362 and the front bottom 360 at obtuse angles. The obtuse angle may be between 110 degrees and 150 degrees. The third front side 366 may be symmetric to the first front side 362 and the fourth front side 368 may be symmetric to the second front side 364. The third front side 366 may be coupled to a side identical to the first side 310 and the fourth front side 368 may be coupled to a side identical to the second side 406.

The bottom 506 may be a rectangular planar surface with a length along the y-axis less than the length of the top 303 along the y-axis and a width along the x-axis equal to the width of the horizontal member 302 along the x-axis. The first side 310 may be a rectangular planar surface in the x-z plane that has a width along the x-axis equal to the length of the horizontal member 302 along the x-axis and a height along the z-axis that is less than the height of the horizontal member 302 along the z-axis. The first side 310 may couple the front 306 to the back 410 and couple the top 303 to the second side 406. The first side 310 may further include the dovetail profiles of the first slot 312, the second slot 314, and the third slot 316. The second side 406 may be a rectangular plane that couples the first side 310 to the bottom 506 and couples the front 306 to the back 410. The second side 406 may have a length along the x-axis equal to the length of the horizontal member 302 and a width such that the second side may couple the first side 310 to the bottom 506 at an obtuse angle.

In one example, the second side 406 may include a first side aperture 502 and a third threaded insert pocket 504. The first side aperture 502 may extend in the z-direction from the second side 406. The first side aperture 502 may extend into the horizontal member 302 at a depth such that the first side aperture 502 does not extend through the top 303. However, the first side aperture 502 may be deep enough that a person handling the calibration phantom holder 300 may place their fingers in the first side aperture 502 to grip the horizontal member 302. The first side aperture 502 may be long enough along the x-axis and long enough along the y-axis to accommodate a person's fingers and may have rounded edges to allow a person to easily grip the first side aperture 502. The third threaded insert pocket 504 may extend into the horizontal member 302 at a depth such that the third threaded insert pocket 504 does not extend through the top 303. In some examples, there may be a fourth threaded insert pocket symmetrical to the third threaded insert pocket 504 across the x-axis. The third threaded insert pocket 504 and the fourth threaded insert pocket may replace the first threaded insert pocket 324 and the second threaded insert pocket 326, in some examples.

The vertical member 304 may be made of the same material as the horizontal member 302. The vertical member may include a front 336, a back 402, a top 338, a first side 344, a second side 346, a third side 516 and a fourth side 518. The vertical member 304 may lie in the z-y plane and have a width along the x-axis that is less than the depth of the horizontal member 302 along the z-axis. In one example, the front 336 may be a second front. The top 338 of the vertical member 304 may have a length along the y-axis that is equal to the length of the horizontal member 302 along the y-axis. The top 338 may be coupled to the first side 344 at a right angle by a first rounded corner 342 and the top 338 may be coupled to the second side 346 at a right angle by a second rounded corner 340. The first side 344 and the second side 346 may be symmetric. The front 336 may be a planar surface in the z-y plane. The front 336 may include a first aperture 350 and a second aperture 352. The first aperture 350 and the second aperture 352 may be identical apertures located symmetrically about a midline of the vertical member 304 along the z-axis. The first aperture 350 and the second aperture 352 may be rounded apertures that extend into the vertical member 304 a distance less than the depth of the vertical member 304 in the x-direction. The front 336 may also include a first handle aperture 348 and a second handle aperture 354. The first handle aperture 348 and the second handle aperture 354 may be identical apertures located symmetrically about a midline of the vertical member 304 along the z-axis. The handle apertures may extend through the entirety of the vertical member 304. The handle apertures may have a length along the z-axis and a width along the y-axis such that a person could insert their fingers through the apertures to hold the calibration phantom holder 300. The handle apertures may have rounded edges to make them comfortable to grip.

The vertical member 304 may include a face 356 which is recessed relative to the front 336, such as shown in FIG. 3. The face 356 may be in face sharing contact with the back 410 of the horizontal member 302, when the vertical member 304 and the horizontal member 302 are coupled, such as shown in FIGS. 5-6. One method to couple the vertical member 304 to the horizontal member 302 includes sliding the first joint 332 and second joint 334 of the horizontal member 302 respectively through the first dovetail inlet 328 and the second dovetail inlet 330, such as shown in FIG. 3. FIG. 4 shows the horizontal member 302 spaced apart from the vertical member 304 in an un-coupled configuration. In some examples, such shown in FIG. 4, the vertical member 304 may include an indent 357. The coupling between the vertical member 304 and the horizontal member 302 may be secured by inserting a threaded insert through a threaded insert pocket in the horizontal member 302, such as the first threaded insert pocket 324, the second threaded insert pocket 326, the third threaded insert pocket 504, or the fourth threaded insert pocket (not shown). Bolts may be coupled to the threaded inserts to couple the vertical member 304 to the horizontal member 302. The bolts may be used to pull the vertical member 304 into contact with the horizontal member 302, such as shown in FIG. 5 and FIG. 6. The back 402 of the vertical member 304 may include a raised portion 520 and a flat portion 522. The flat raised portion 520 may include a portion of the back 402 that extends further in the +x direction than the flat portion 522. The raised portion may be formed of a first rectangular portion 524 that surrounds the first handle aperture 348 and a second rectangular portion 526 that surrounds the second handle aperture 354. The first rectangular portion 524 may be coupled to the second rectangular portion 526 by a third rectangular portion 528. The third rectangular portion 528 may lie parallel to the top 338. The back 410 may further include a first joint cover 530 and a second joint cover 532. The joint covers may include raised portions of the back 410 that extend along the +x axis. The first joint cover 530 may surround the position of the second joint 334 and the second joint cover 532 may surround the position of the first joint 332. The back 402 may further include a plurality of coupling apertures including a first coupling aperture 508, a second coupling aperture 510, a third coupling aperture 512 and a fourth coupling aperture 514. These coupling apertures may be circular apertures that extend from the back 402 to the front 336 of the vertical member 304. The coupling apertures may have a diameter sized to accommodate a screw or other fastener that may allow the vertical member 304 to the horizontal member 302. In some examples the inside of the coupling apertures may be threaded to couple the vertical member 304 to a screw. The back 402 may further include a set of three apertures; a first aperture 540, a second aperture 542, and a third aperture 544. In some examples, the vertical member 304 may include a hanger 404, as shown in FIG. 4. The hanger 404 may extend in the +x direction from the back and include a hook that extends in the −z direction. The hanger 404 may be used to couple the vertical member 304 to an attachment plate of a table interface.

FIG. 6 depicts the calibration phantom holder 300 coupled to a cradle clamping holder 600. Some elements of the calibration phantom holder 300 that are introduced with respect to FIGS. 3-5 may not be labeled and/or reintroduced in FIGS. 6, for brevity. The cradle clamping holder 600 is one example of the support system 116 described above with reference to FIG. 1. The cradle clamping holder 600 comprises a planar body 602. The planar body 602 may have an elongated rectangular shape. The planar body 602 is a single, continuous body. The planar body 602 may be formed of a metal, a plastic, and/or a combination of rigid materials. The planar body 602 may include one or more cutouts 612 that extend through a thickness of the planar body 602. The one or more cutouts 612 may be included to reduce a weight of the cradle clamping holder 600 while retaining a structural integrity of the planar body 602. The planar body 602 further includes one or more through holes 616 that extend through the thickness of the planar body 602. One or more through holes 616 are positioned towards the second end 696 of the cradle clamping holder 600, and thus of the planar body 602. Additionally, a through hole 616 is positioned towards a first end 692 of the cradle clamping holder 600. Each of the through holes 616 may be used to position leveling features of the planar body 602, as such as a level sensor or level lines configured to identify the position of the cradle clamping holder 600 in space.

The cradle clamping holder 600 includes a first leveling foot 622a and a second leveling foot 622b, each of which include a rod 624 that extends through the hole 616 that extends through the thickness of the planar body 602 perpendicular to the planar surface of the planar body 602. The rod 624 and the hole 616 may each be threaded to allow the rod to rotatably couple to the hole 616. A position of the planar body 602 along the length of each of the rod 624 of the first leveling foot 622a and the second leveling foot 622b is independently adjustable, as further described herein. The first leveling foot 622a and the second leveling foot 622b have the same configuration, and thus description of the first leveling foot 622a is to be understood as also describing the second leveling foot 622b, unless otherwise noted. Each leveling foot may include an adjustable head that can be rotated.

Rotation of the adjustable head of the first leveling foot 622a may move the planar body 602 along the length of the rod 624 of the first leveling foot 622a. For example, rotation of the adjustable head in a clockwise direction may move the first leveling foot 622a (e.g., the rod 624) downwards, with respect to the planar body 602. Moving the first leveling foot 622a downwards with respect to the planar body 602 results in an increasing portion of the length of the rod 624 being positioned below the planar body 602, and a decreasing portion of the length of the rod 624 being positioned above the planar body 602. Increasing the portion of the length of the rod 624 positioned below the planar body 602 may increase a vertical distance between the planar body 602 and a surface on which the planar body 602 is positioned, such as a cradle of an imaging system.

The cradle clamping holder 600 further comprises a coupling clamp 640 at the first end 692 of the cradle clamping holder 600. The coupling clamp 640 includes a handle 656, which may be used to hold, carry, adjust, and otherwise position the cradle clamping holder 600. The coupling clamp 640 is formed of a support beam 644 with a first clamp 642a and a second clamp 642b. The support beam 644 is positioned perpendicular to the length of the planar body 602, such that the first clamp 642a and the second clamp 642b are positioned on either side of the planar body 602. The first clamp 642a and the second clamp 642b are each coupled to the support beam 644 at a pivot joint 646. Each of the first clamp 642a and the second clamp 642b are adjustable between a first position and a second position. Adjustment between the first position and the second position enable the first clamp 642a and the second clamp 642b to be used to clamp the cradle clamping holder 600 to a surface, such as a cradle of an imaging system 100. The first clamp 642a and the second clamp 642b have the same configuration, and thus description of the first clamp 642a is to be understood as also describing the second clamp 642b, unless otherwise noted.

The coupling clamp 640 is coupled to the planar body 602 at the first end 692 of the planar body 602 via a swivel joint 660. The swivel joint 660 may selectively couple the coupling clamp 640 to the planar body 602. The swivel joint 660 enables rotation of the planar body 602 about the central axis with respect to the coupling clamp 640. Described another way, the coupling clamp 640 may be stationary (e.g., may not move with respect to the central axis) and the planar body 602 may tilt side to side with respect to the central axis. In conjunction with adjustment of the first leveling foot 622a and the second leveling foot 622b, the swivel joint 660 enables leveling of the cradle clamping holder 600.

An attachment plate 630 configured to support an imaging subject is directly or indirectly coupled to the planar body 602 at the second end 696 of the planar body 602, opposite the first end 692. For example, the attachment plate 630 may be directly coupled to the planar body 602 via a weld, braze, or other coupling method that renders the attachment plate 630 and the planar body 602 as a singular, continuous feature. In another example, the attachment plate 630 is indirectly coupled to the planar body 602, such as via one or more adjustable rods. The one or more adjustable rods may be removably attached to the planar body 602 at a first end of a rod and be removably attached to the attachment plate 630 at a second end of the rod. For example, the one or more adjustable rods may be attached to the planar body 602 and the attachment plate 630 via snap fitting, a threaded attachment, and/or other removable attachment mechanisms. The one or more rods may be interchangeable, and thus adjustable. The attachment plate 630 may have various configurations that enable the cradle clamping holder 600 to support an imaging subject via the attachment plate 630 and/or via a mounting attachment selectively coupled to the attachment plate 630. In the example cradle clamping holder 600 shown in FIG. 6, the attachment plate 630 comprises multiple cutouts 632 and through holes 634, which may be included to reduce a weight of the cradle clamping holder 600 while retaining a structural integrity of the attachment plate 630. The cutouts 612 and through holes 616 may further provide features via which a mounting attachment may be coupled to the attachment plate 630. In one example, a fastener may be inserted through the through the hole 634 or the cutouts 632 that may couple to a mating hole in the vertical member 304 to couple the attachment plate 630 the to the back 402 of the vertical member 304. In some examples, the attachment plate 630 may be coupled to the back 402 of the vertical member 304 by a hook, such as the hanger 404 shown in FIG. 4.

As the attachment plate 630 is coupled to the vertical member 304, movement of the planar body 602 translates to movement of the vertical member 304 and, by extension, movement of the calibration phantom holder 300. For example, adjustment of one or more of the first leveling foot 622*a* and the second leveling foot 622*b* to adjust a vertical position of the planar body 602 also adjusts a vertical position of the vertical member 304.

The coupling clamp 640 is configured to mate with a cradle of an imaging system, center the cradle clamping holder 600 with respect to the cradle, and fix a position of the planar body 602 relative to the cradle. The first leveling foot 622*a*, the second leveling foot 622*b*, and a swivel joint 660 are configured to adjust a leveling of the cradle clamping holder 600 when positioned on the cradle.

Figure 7:
FIG. 7 shows a side view of a second example of a calibration phantom holder with a slab of material coupled thereto, according to embodiments of the present disclosure.
Figure 7:
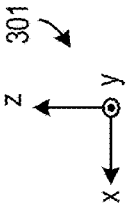

FIG. 7 is a schematic diagram showing a calibration phantom holder 700 supporting a phantom 702. The calibration phantom holder 700 may be similar to calibration phantom holder 300 of FIGS. 3-6. Elements of calibration phantom holder 700 that are shared with the calibration phantom holder 300 are numbered the same and will not be reintroduced in FIG. 7, for brevity.

The phantom 702 may be a rectangular prism in shape, with a front face 704 and back face identical to the front face 704 that lie in the x-z plane, a top 710 and a bottom 712 that lie in the x-y plane, and first side 714 and a second side 716 that lie in the y-z plane. The first side 714 and the second side 716 may be rectangular in shape and have a length along the y axis equal that may be less than or equal to the length of the top 303 along the y-axis. The first side 714 and the second side 716 may have a height along the z-axis. The height of the phantom 702 may fall within a range, such as from 1 cm to 10 cm, and a technician may stack combinations of one or more of the phantoms during a calibration process. The top 710 and the bottom 712 may have a length along the y-axis equal to the length of the first side 714 and second side 716 along the y-axis. The top 710 and bottom 712 may have a width along the x-axis equal to the width of the fourth top surface 322. The bottom 712 may be in face sharing contact with the fourth top surface 322.

The bottom 712 may include a tab 708. The tab 708 may extend in the −z direction from the bottom 712 and may be located a small distance in the +x direction from the second side 716. The portion of the bottom 712 of the phantom 702 that lies in the −x direction from the tab 708 may be in face sharing contact with the third top surface 320. The tab 708 may span the length of the phantom 702 along the y-axis, and have a shape, a width along the x-axis and a height along the z-axis such that the tab 708 can couple to the third slot 316. In the example shown in FIG. 7, the tab 708 has a rectangular profile identical to the rectangular profile of the third slot 316. However, in other examples, the third slot 316 may have a dovetailed profile and the tab 708 may have a dovetailed shape to match the profile of the third slot 316.

In the example shown in FIG. 7 the phantom 702 is coupled to the third slot 316. However, the first slot 312, the second slot 314, and the third slot 316 may be identical in shape and size, which may allow a phantom such as the phantom 702 to be inserted into any of the slots. The top 710 includes a top slot 706 identical in shape and size to the third slot 316. A second phantom similar to the phantom 702 that includes a tab such as the tab 708 may be stacked on top of the top 710 and secured by inserting the tab of the second phantom into the top slot 706 of the phantom 702. In this way, a stack of one or more phantoms may be formed on top of the fourth top surface 322. The phantoms within a stack may be made of different materials and in some examples may have different heights along the z-axis. However, the phantoms may each include a tab such as the tab 708 and a top slot such as the top slot 706 to allow the phantoms to be stacked in any order. FIG. 7 includes an alternate example of the coupling between the vertical member 304 and the horizontal member 302. In this example, the vertical member 304 is stacked on top of the horizontal member 302 and may be coupled to the horizontal member 302 by a fastening method such as a mating slot and tab, or fasteners such as a bolts or screws.

FIG. 8 is an example calibration phantom holder 800 that includes guiding features for reproducible positioning of the calibration phantoms. Calibration phantom holder 800 may be similar to the calibration phantom holder 300 of FIGS. 3-6. Elements of the calibration phantom holder 800 that are shared with the calibration phantom holder 300 are numbered the same and will not be reintroduced in FIG. 8, for brevity.

The calibration phantom holder 800 includes a plurality of rods 810. The rods 810 may include a first rod 802, a second rod 804, a third rod 806, and a fourth rod 808. The first rod 802 and the second rod 804 may be coupled to the second top surface 318. The first rod 802 and the second rod 804 may be arranged in the center of the second top surface 318 with respect to the width of the second top surface 318 along the x-axis and may be evenly spaced from the center of the second top surface 318 with respect to the length of the second top surface 318. The third rod 806 and the fourth rod 808 may be arranged in the center of the third top surface 320 with respect to the width of the third top surface 320 along the x-axis and may be evenly spaced from the center of the third top surface 320 with respect to the length of the third top surface 320 along the y-axis. In some examples, there may be rods positioned in a similar manner on the fourth top surface 322. The rods 810 may have a height along the z-axis that may be equal to or greater than the height of a stack of phantoms placed upon the top 303. The rods 810 may be cylindrical in shape or they may be a prism of another shape. The rods 810 may have a width that is less than the height of the rods 810. The rods may be shaped to couple to a mating hole in one or more phantoms. The rods may be inserted through the holes of one or more phantoms stacked on the top 303 of the calibration phantom holder 300 to provide stability to the stack. In some examples, the rods may be made of acrylic, PVC, or PE.

FIG. 9 shows a schematic diagram 900 of a cross sectional view of an example set of rods inserted through an example phantom 912. The phantom 912 may be comprised of three segments. There may be a first segment 904 that is separated from a second segment 902 by a first aperture 914 and a third segment 906 that is separated from the second segment 902 by a second aperture 916. There may be a first rod 908 that may be inserted through the first aperture 914 and there may be second rod 910 that may be inserted through the second aperture 916. The rods may have a height greater than that of the phantom 912 such that they extend through the top and/or bottom of the phantom 912 when the rods are inserted through the apertures. The apertures may be sized accordingly to accommodate the size and shape of the rods an allowance so that the rods may be inserted and removed easily. When inserted through one or more phantoms, the rods may prevent the phantoms from moving during a scan and increase the clarity of the resulting image and calibration.

Figure 10:
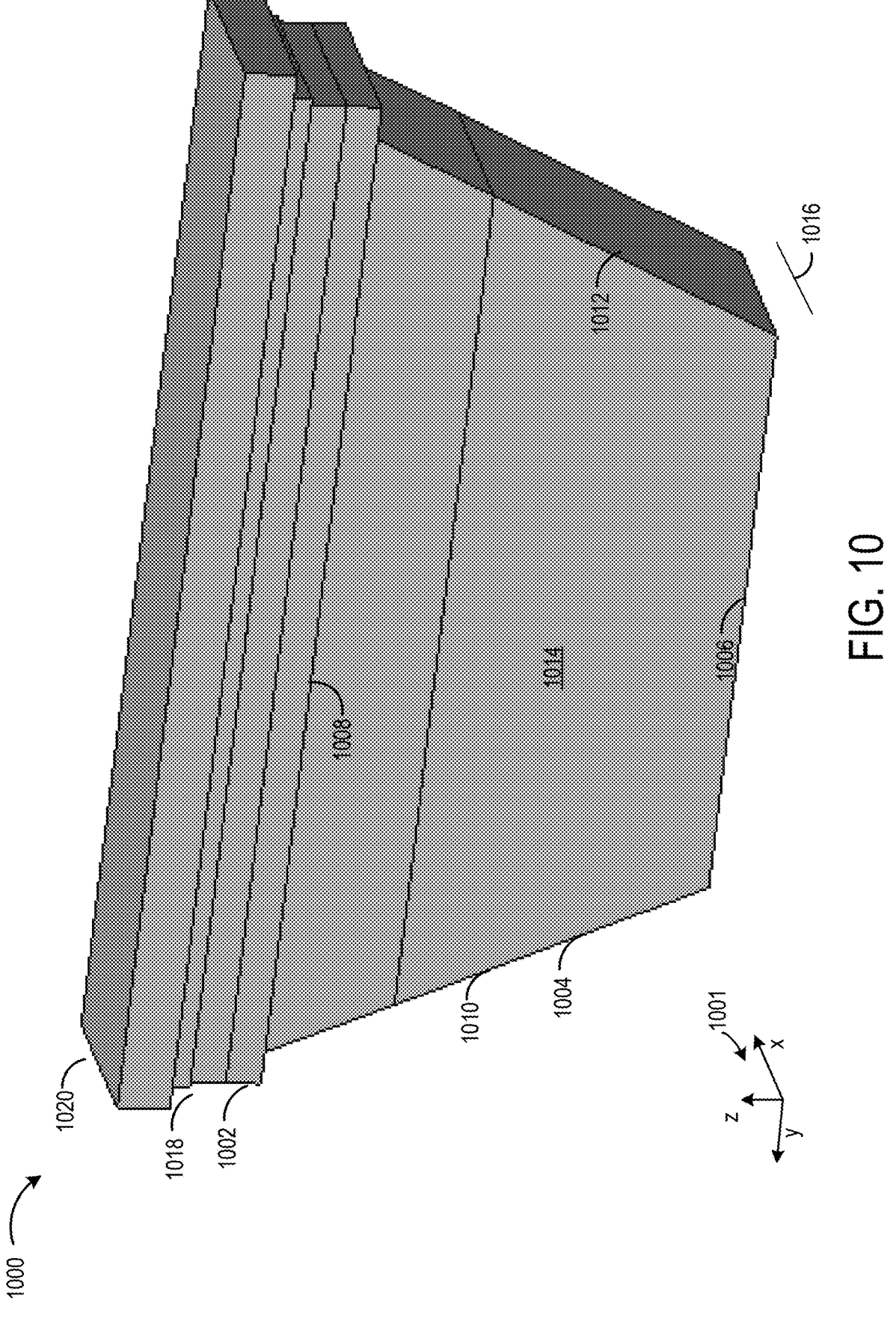
FIG. 10 shows a perspective view of a first phantom, according to embodiments of the present disclosure.
Figure 11:
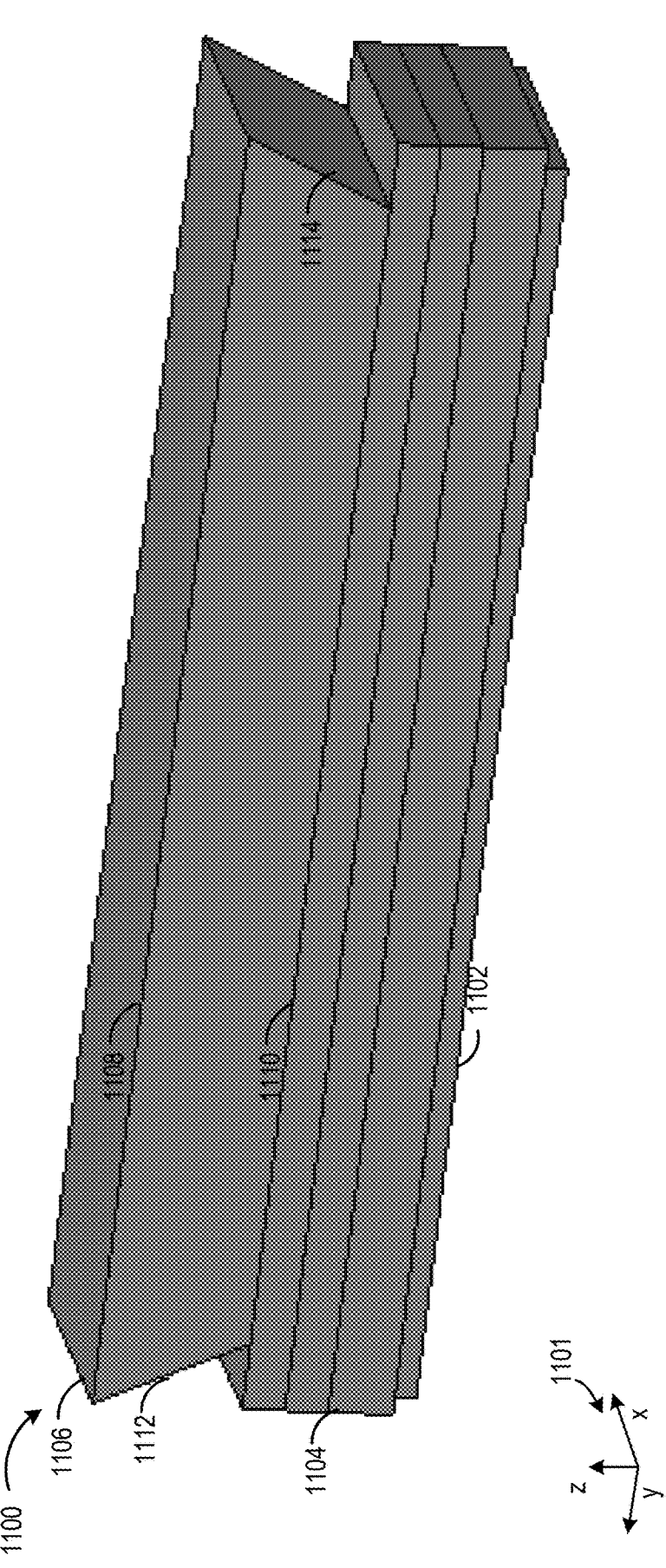
FIG. 11 shows a perspective view of a second phantom, according to embodiments of the present disclosure.

FIGS. 10 and 11 are diagrams of example phantoms. The example phantoms may be used to calibrate a PCCT system, where the example phantoms are positioned into the bore of the PCCT system supported by the disclosed calibration phantom holder, such as the calibration phantom holder 300 depicted in FIGS. 3-6, or the holders depicted in FIGS. 7-8. The example phantoms depicted in FIGS. 10 and 11 may be configured to mate with the channels on the horizontal member 302 of the calibration phantom holder 300 and may be slid in from the side, in a similar method of insertion to the insertion method of the phantom 702 described with respect to FIG. 7.

FIG. 10 is a diagram of a first example phantom 1000. FIG. 10 includes a Cartesian coordinate system 1001. The z-axis of coordinate system 1001 may be a vertical axis (e.g., parallel to a gravitational axis), the y-axis of coordinate system 1001 may be a longitudinal axis (e.g., horizontal axis), and/or the x-axis of coordinate system 1001 may be a lateral axis, in one example. However, the axes may have other orientations, in other examples. When referencing direction, positive may refer to in the direction of the arrow of the x-axis, y-axis, and z-axis and negative may refer to in the opposite direction of the arrow of the x-axis, y-axis, and z-axis. A filled circle may represent an arrow and axis facing toward, or positive to, a view. An unfilled circle may represent an arrow and an axis facing away, or negative to, a view. Further, FIG. 10 is drawn to scale, though other relative dimensions could be used if desired.

The first example phantom 1000 may have a base 1004. The base 1004 may be trapezoidal prism in shape, with a bottom 1006 parallel to a top 1008. The bottom 1006 may have a shorter length along the y-axis than the top 1008. There may be a first angled side 1010 and a second angled side 1012 that couple the bottom 1006 to the top 1008. The base 1004 may have a trapezoidal planar front face 1014. The base 1004 may have a width 1016 along the x-axis.

There may be a first rectangular prism 1002 coupled to the top 1008 of the base 1004. The first rectangular prism may have the same width 1016 along the x-axis as the base 1004. The length of the first rectangular prism 1002 along the y-axis may be greater than the length of the base 1004 along the y-axis to create an overhang. There may be a second rectangular prism 1018 coupled to the top of the first rectangular prism 1002. The second rectangular prism may have a slightly greater length along the y-axis than the first rectangular prism 1002 and may have the same width as the first rectangular prism 1002. There may be a third rectangular prism 1020 that is coupled to the top of the second rectangular prism 1018. The third rectangular prism may have a width along the x-axis that is greater than the width of the second rectangular prism 1018 and a length along the y-axis that is greater than the width of the second rectangular prism 1018 along the y-axis. In one example, each layer of the example phantom 1000, e.g., the base 1004, the first rectangular prism 1002, the second rectangular prism 1018, etc., may constitute a slab, such as one of the slotted slabs described with reference to FIG. 7. For example, one or more of the layers, e.g., slabs, may be added or removed during the calibration process based on the calibration method implemented by the technician FIG. 11 is a diagram of a second example phantom 1100. FIG. 11 includes a Cartesian coordinate system 1001. The z-axis of coordinate system 1101 may be a vertical axis (e.g., parallel to a gravitational axis), the y-axis of coordinate system 1101 may be a longitudinal axis (e.g., horizontal axis), and/or the x-axis of coordinate system 1101 may be a lateral axis, in one example. However, the axes may have other orientations, in other examples. When referencing direction, positive may refer to in the direction of the arrow of the x-axis, y-axis, and z-axis and negative may refer to in the opposite direction of the arrow of the x-axis, y-axis, and z-axis. A filled circle may represent an arrow and axis facing toward, or positive to, a view. An unfilled circle may represent an arrow and an axis facing away, or negative to, a view. Further, FIG. 10 is drawn to scale, though other relative dimensions could be used if desired.

The second example phantom 1100 may have a base 1102. The base 1102 may be a rectangular prism with a length along the y-axis, a width along the x-axis and a height along the z-axis. There may be a rectangular prism 1104 coupled to the top of the base 1102. The rectangular prism 1104 may have a greater height along the z-axis than the base 1102, a greater length along the y-axis than the base 1102, and a greater width along the x-axis than the base 1102. In one example the rectangular prism 1104 may be comprised of a plurality of layers, where each layer is a slab that may comprise a different thickness, density, or other clinically relevant parameter.

There may be a trapezoidal prism 1106 coupled to the top of the rectangular prism 1104. The trapezoidal prism may have a bottom 1110 that is shorter in length along the y-axis than the length along the y-axis of a top 1108. There may be a first slanted side 1112 and a second slanted side 1114 that couple the top 1108 to the bottom 1110.

FIG. 12 and FIG. 13 are flowcharts describing a respective method 1200 and a method 1300 for using a calibration phantom holder to perform a calibration of a PCCT system. The method 1200 and the method 1300 are described with respect to the calibration phantom holder 300 of FIGS. 3-6. The PCCT system be the imaging system 100 or the imaging system 200, respectively described with reference to FIGS. 1-2.

At 1202 the method 1200 includes mounting the calibration phantom holder to a support system of the imaging system. In one example, the calibration phantom holder may be coupled to a cradle clamping holder such as cradle clamping holder 600. The cradle clamping holder may allow the calibration phantom holder to be coupled to the cradle of the patient table of the PCCT system.

At 1204 the method 1200 may include preparing one or more calibration phantoms. To prepare the one or more calibration phantoms, at 1206, the method 1200 may include selecting a plurality of slotted slabs, and slotting one or more slotted slabs of the plurality of slotted slabs into one or more parallel slots of the horizontal member of the calibration phantom holder. The slotted slabs may be made of different materials and have different dimensions. A combination of slotted slabs may be selected and ordered to create a stack that reflects the clinical goals of the PCCT system and the corresponding features of a stack used to calibrate the PCCT system. The method may further include arranging one or more of the plurality of slotted slabs in one or more horizontal sections and vertically stacking one or more of the plurality of slotted slabs in a vertical stack in the one or more horizontal sections. To form a vertical stack, the slabs may be slid into the slots included on the top of other slabs. In some examples, rods may be inserted into apertures in the slabs to provide stability to the vertical stack, such as shown in the example calibration phantom holder 800 in FIG. 8. Vertical stacks of calibration phantoms may be formed on one or more of the top surfaces included in the top of the horizontal member of the calibration phantom holder.

In one example, the one or more calibration phantoms may be prepared based on a calibration operation. The calibration operation may be output automatically by a controller of the PCCT system (e.g., computer or computing device 216) in response to a user selection, and may include user instructions displayed on a display device (e.g., display 232). For example, the user instructions may include the number of slotted slabs, slab dimensions, slab materials, a stacking order of slabs, position on the horizontal member, etc. The user instructions may be followed by a human operator, e.g., the technician, to prepare the one or more calibration phantoms.

At 1208, the method 1200 may include positioning the calibration phantom holder in the bore of the imaging system. The calibration phantom holder may be coupled to the cradle of the patient table by the cradle clamping holder. The position of the patient table may be adjusted to maneuver the calibration phantom holder into the bore of the imaging system. At 1210, the method 1200 may include performing a calibration operation according to the method described with respect to FIG. 13.

Turning to FIG. 13, the method 1300 is described by which a calibration may be performed on phantoms assembled on the calibration phantom holder. At 1302 the method 1300 may include obtaining instructions as to the calibration operation. As described above, the calibration operation may be output automatically by the controller of the PCCT system in response to the user selection, and displayed on the display device the PCCT system. In one example, the calibration operation may include a scanning order of the vertical stacks on the calibration phantom holder, which may be executed automatically. The calibration phantom holder may include more than one stack, and each stack may include more than one slotted slab. The contents of each stack may be altered by removing one or more slabs between scans. The displayed calibration operation may include instructions for the technician during the scan, such as a plan of how and when to adjust vertical stacks (e.g., remove or add slabs) between scans, and how many scans will be performed on each stack.

At 1304 the method may include positioning a calibration phantom, e.g., a vertical stack, in the path of the X-ray beam. This may include adjusting the position of the patient table to place one stack assembled on the calibration phantom holder in the path of the X-ray beam. In some examples, the patient table may be moved according to a predetermined method that accounts for the position of each stack relative to the patient table and automatically centers a stack selected according to the instructions obtained at 1302.

At 1306, the method may include scanning the vertical stack. This may include the PCCT system firing an X-ray beam at the vertical stack. The X-ray beam may be attenuated by the calibration phantom and the attenuated X-ray beam may be measured by a detector array. The measured response of the detector array to the attenuated X-ray beam may be stored and the data may be used to assemble one or more images of the calibration phantoms. The resulting images may be analyzed and used to adjust settings of the PCCT system to calibrate the PCCT system.

At 1308, the method 1300 may include determining if all of the slabs have been removed that have been specified to be removed in the instructions obtained at 1302. In some examples, the instructions obtained at 1302 may include directions to scan a full stack of slabs, then to remove one or more slabs and scan again. The instructions may further include incrementally removing slabs and scanning the stack. At 1308, the method includes checking that all of the phantoms have been removed from the stack, which signals that the calibration process performed on the stack has been completed. In one example, a human operator, may visually inspect the calibration phantom holder to determine if all of the phantoms have been scanned according to the instructions obtained at 1302 and may provide feedback to a computing system that may control the scan process. In another example, a computer or operating system connected to the PCCT system may determine if all scans on the vertical stack have been completed. If all of the specified calibration phantoms have not been removed at 1308, the method 1300 may include 1314. At 1314, the method 1300 may include a human operator removing one or more calibration phantoms from the stack according to the instructions obtained at 1302. The instructions 1302 may be displayed to the operator via a monitor or other display, which may prompt them to adjust the composition of each stack according to the instructions between scans.

If all of the specified calibration phantoms have been removed at 1308, the method 1300 may include 1310. At 1310, the method 1300 may include determining if all specified stacks have been scanned. In one example, a computer or operating system connected to the PCCT system may determine if all of the specified stacks have been scanned. If all of the specified stacks have not been scanned at 1310, the method 1300 may include adjusting the position of the calibration phantom holder to center a specified stack that has not been scanned yet. This may be accomplished by moving the patient table. There may be preset positions stored with in a computer system associated with the position of the patient table to center each vertical stack within the X-ray beam. If all specified stacks have been scanned at 1310, the method 1300 may include 1312. At 1312 the method 1300 may include indicating the calibration scans have been completed. The indication may be registered by a computer system coupled to the PCCT system and may be used to indicate that the detector array or other portions of the PCCT system may be powered down.

An exemplary calibration operation according to the methods disclosed herein may include preparing a first calibration phantom comprising a first plurality of slotted slabs arranged in a first vertical stack and preparing a second calibration phantom comprising a second plurality of slotted slabs arranged in a second vertical stack. The second vertical stack may be positioned adjacent to the first vertical stack, such as arranged in a horizontal section next to the first vertical stack. The calibration operation may include scanning the first calibration phantom, and then scanning the second calibration phantom. Subsequently, the calibration operation may include preparing a third calibration phantom comprising a third plurality of slotted slabs arranged in the first vertical stack, the third calibration phantom prepared by removing or adding one or more slotted slabs to the first calibration phantom, and scanning the third calibration phantom.

FIG. 14 shows an imaging system 1400 including an example of the cradle 120, the support system 116, and the calibration phantom holder 300 supporting one or more calibration phantoms 1402. Some elements of the imaging system 1400 that are introduced with respect to FIGS. 1-6 may not be labeled and/or reintroduced in FIG. 14, for brevity.

In the example, the calibration phantom holder 300 is coupled to the support system 116, which is itself supported by the cradle 120 of the table 114. The calibration phantom holder 300 may be loaded with the one or more of calibration phantoms 1402 comprising one or more slabs. As the example shows, the open platter design of calibration phantom holder 300 allows for positioning multiple vertical stacks of slabs arranged horizontally side by side. The loaded holder may then be adjusted to into the bore 124, whereupon each vertical stack may be scanned. The slabs being accessible from either side of the holder allows for easy changing of individual slabs, which, as described above, may include sliding one or more slabs off from or onto one or more of the vertical stacks. The calibration phantom holder 300 is robust, and supports substantial weight demanded by slab phantom calibration procedures. At the same time, the overall footprint of the calibration phantom holder 300 is small enough to fit within the circumference of the bore.

Figure 15:
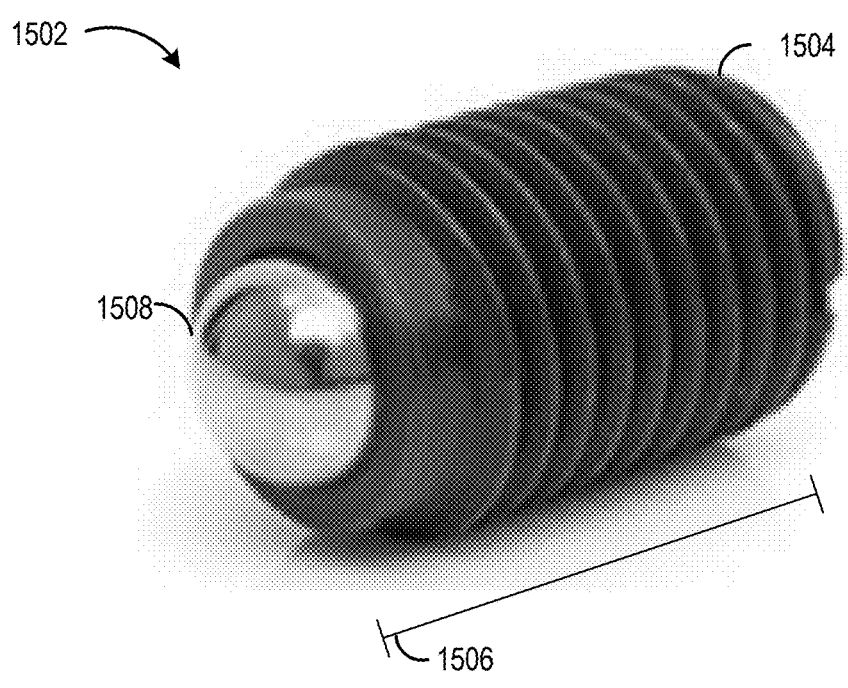
FIG. 15 is a perspective view of an example detent for a calibration phantom holder; according to embodiments of the present disclosure.

FIG. 15 includes an image of an example detent 1502. The detent 1502 may have a threaded body 1504. The threaded body 1504 may be cylindrical in shape and have raised threads extending along the circumference of the cylindrical body. The threaded body 1504 may be configured to be securely inserted in a channel such as the first slot 312 described with respect to FIG. 3. The threaded body may have a length 1506 that may be aligned parallel to the y-axis when the detent 1502 is inserted in a channel. The detent 1502 may include a rounded cap 1508 coupled to a circular face of the threaded body 1504. The rounded cap 1508 may be semispherical and made of a metal or plastic. The rounded cap 1508 may be configured to make contact with a phantom such as phantom 702 when the phantom is inserted into a channel. The threaded body 1504 may prevent the detent from changing position within the channel when the phantom is inserted, and so the phantom may be prevented from being inserted past the position of the rounded cap 1508 within the channel. This may allow a phantom to be inserted at the same position within a channel during each scan.

In this way, by providing a calibration phantom holder which supports easily interchangeable, modular calibration phantoms, the disclosed approach increases the efficiency of PCCT system calibration over existing approaches.

Though a photon counting computed tomography (PCCT) system is described by way of example, it should be understood that the present techniques may also be useful when applied to other X-ray imaging modalities having photon counting detectors, such as X-ray angiography systems, X-ray tomosynthesis systems, X-ray mammography systems, X-ray fluoroscopy systems, X-ray interventional systems, X-ray C-arm systems, etc. The present discussion of a PCCT imaging modality is provided merely as an example of one suitable imaging modality.

The disclosure also provides support for a calibration phantom holder for an imaging system comprising: a horizontal member comprising a plurality of parallel slots distributed along an upper surface of the horizontal member, each parallel slot of the plurality of parallel slots configured to support one or more calibration phantoms, and a vertical member perpendicularly coupled to the horizontal member, the vertical member configured to couple to a support system of the imaging system. In a first example of the system, the calibration phantom holder comprises a nonmetallic material. In a second example of the system, optionally including the first example, the one or more calibration phantoms comprise a slotted slab. In a third example of the system, optionally including one or both of the first and second examples, the horizontal member is configured to support a plurality of slotted slabs arranged vertically one on top of another. In a fourth example of the system, optionally including one or more or each of the first through third examples, the horizontal member is configured to support a plurality of slotted slabs arranged horizontally side by side. In a fifth example of the system, optionally including one or more or each of the first through fourth examples, the horizontal member is configured to support a plurality of slotted slabs arranged horizontally side by side and vertically one on top of another. In a sixth example of the system, optionally including one or more or each of the first through fifth examples, each parallel slot of the plurality of parallel slots includes one or more detents. In a seventh example of the system, optionally including one or more or each of the first through sixth examples, each parallel slot of the plurality of parallel slots has a dovetailed profile. In a eighth example of the system, optionally including one or more or each of the first through seventh examples, the vertical member comprises one or more apertures configured to act as handles and is configured to couple to a cradle clamping holder, and the horizontal member comprises one or more apertures configured to act as handles. In a ninth example of the system, optionally including one or more or each of the first through eighth examples, the horizontal member comprises a first front and a back, the first front and the back being hexagonal in shape, and wherein the vertical member comprises a second front and a face, the face being recessed relative to the second front, and wherein the face of the vertical member is perpendicularly coupled to the back of the horizontal member. In a tenth example of the system, optionally including one or more or each of the first through ninth examples, the vertical member is perpendicularly coupled to the back of the horizontal member by a first dovetail inlet including a first joint and a second dovetail inlet including a second joint, and wherein the back of the horizontal member comprises a first joint cover and a second joint cover, the first joint cover positioned over the first joint and the second joint cover positioned over the second joint.

The disclosure also provides support for an imaging system comprising: a cradle, a support system, a calibration phantom holder comprising a horizontal member with a plurality of parallel slots distributed along an upper surface of the horizontal member, and a vertical member perpendicularly coupled to the horizontal member, and one or more calibration phantoms configured to be supported by the plurality of parallel slots. In a first example of the system, the one or more calibration phantoms comprise a slotted slab with an upper slot and a lower tab, the lower tab configured to slide into a corresponding slot of the plurality of parallel slots and the upper slot configured to support a second calibration phantom. In a second example of the system, optionally including the first example, the slotted slab is configured to be one or both of stacked vertically one on top of the other and arranged horizontally side by side. In a third example of the system, optionally including one or both of the first and second examples, the slotted slab comprises an aperture configured to receive a rod inserted vertically through a stack, and wherein the rod is coupled to the horizontal member.

The disclosure also provides support for a method for a calibration phantom holder for an imaging system comprising: mounting a vertical member of the calibration phantom holder to a support system of the imaging system, preparing one or more calibration phantoms, positioning the calibration phantom holder into a bore of the imaging system, and performing a calibration operation with the one or more calibration phantoms, wherein preparing one or more calibration phantoms includes selecting a plurality of slotted slabs, and slotting one or more slotted slabs of the plurality of slotted slabs into one or more parallel slots of a horizontal member of the calibration phantom holder. In a first example of the method, performing the calibration operation comprises scanning the one or more calibration phantoms in a sequential order. In a second example of the method, optionally including the first example, the method further comprises: arranging one or more of the plurality of slotted slabs in one or more horizontal sections and vertically stacking one or more of the plurality of slotted slabs in a vertical stack in the one or more horizontal sections. In a third example of the method, optionally including one or both of the first and second examples, the method further comprises: preparing a first calibration phantom comprising a first plurality of slotted slabs arranged in a first vertical stack, preparing a second calibration phantom comprising a second plurality of slotted slabs arranged in a second vertical, scanning the first calibration phantom, scanning the second calibration phantom, preparing a third calibration phantom comprising a third plurality of slotted slabs arranged in the first vertical stack, the third calibration phantom prepared by removing or adding one or more slotted slabs to the first calibration phantom, and scanning the third calibration phantom. In a fourth example of the method, optionally including one or more or each of the first through third examples, the calibration phantom holder comprises a base material used in the calibration operation.

FIGS. 3 through 11 and 14 through 16 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A calibration phantom holder for an imaging system comprising:
   a horizontal member comprising a plurality of parallel slots distributed along an upper surface of the horizontal member, each parallel slot of the plurality of parallel slots configured to support one or more calibration phantoms; and
   a vertical member perpendicularly coupled to the horizontal member, the vertical member configured to couple to a support system of the imaging system.

2. The calibration phantom holder of claim 1, wherein the calibration phantom holder comprises a nonmetallic material.

3. The calibration phantom holder of claim 1, wherein the one or more calibration phantoms comprise a slotted slab.

4. The calibration phantom holder of claim 3, wherein the horizontal member is configured to support a plurality of slotted slabs arranged vertically one on top of another.

5. The calibration phantom holder of claim 3, wherein the horizontal member is configured to support a plurality of slotted slabs arranged horizontally side by side.

6. The calibration phantom holder of claim 3, wherein the horizontal member is configured to support a plurality of slotted slabs arranged horizontally side by side and vertically one on top of another.

7. The calibration phantom holder of claim 1, wherein each parallel slot of the plurality of parallel slots includes one or more detents.

8. The calibration phantom holder of claim 1, wherein each parallel slot of the plurality of parallel slots has a dovetailed profile.

9. The calibration phantom holder of claim 1, wherein the vertical member comprises one or more apertures configured to act as handles and is configured to couple to a cradle clamping holder, and the horizontal member comprises one or more apertures configured to act as handles.

10. The calibration phantom holder of claim 1, wherein the horizontal member comprises a first front and a back, the first front and the back being hexagonal in shape, and wherein the vertical member comprises a second front and a face, the face being recessed relative to the second front, and wherein the face of the vertical member is perpendicularly coupled to the back of the horizontal member.

11. The calibration phantom holder of claim 10, wherein the vertical member is perpendicularly coupled to the back of the horizontal member by a first dovetail inlet including a first joint and a second dovetail inlet including a second joint, and wherein the back of the horizontal member comprises a first joint cover and a second joint cover, the first joint cover positioned over the first joint and the second joint cover positioned over the second joint.

12. An imaging system comprising:
a cradle;
a support system;
a calibration phantom holder comprising a horizontal member with a plurality of parallel slots distributed along an upper surface of the horizontal member, and a vertical member perpendicularly coupled to the horizontal member; and
one or more calibration phantoms configured to be supported by the plurality of parallel slots.

13. The imaging system of claim 12, wherein the one or more calibration phantoms comprise a slotted slab with an upper slot and a lower tab, the lower tab configured to slide into a corresponding slot of the plurality of parallel slots and the upper slot configured to support a second calibration phantom.

14. The imaging system of claim 13, wherein the slotted slab is configured to be one or both of stacked vertically one on top of the other and arranged horizontally side by side.

15. The imaging system of claim 13, wherein the slotted slab comprises an aperture configured to receive a rod inserted vertically through a stack, and wherein the rod is coupled to the horizontal member.

16. A method for a calibration phantom holder for an imaging system comprising:
mounting a vertical member of the calibration phantom holder to a support system of the imaging system;
preparing one or more calibration phantoms;
positioning the calibration phantom holder into a bore of the imaging system; and
performing a calibration operation with the one or more calibration phantoms,
wherein preparing one or more calibration phantoms includes selecting a plurality of slotted slabs, and slotting one or more slotted slabs of the plurality of slotted slabs into one or more parallel slots of a horizontal member of the calibration phantom holder.

17. The method of claim 16, wherein performing the calibration operation comprises scanning the one or more calibration phantoms in a sequential order.

18. The method of claim 16, further comprising arranging one or more of the plurality of slotted slabs in one or more horizontal sections and vertically stacking one or more of the plurality of slotted slabs in a vertical stack in the one or more horizontal sections.

19. The method of claim 18, further comprising preparing a first calibration phantom comprising a first plurality of slotted slabs arranged in a first vertical stack, preparing a second calibration phantom comprising a second plurality of slotted slabs arranged in a second vertical, scanning the first calibration phantom, scanning the second calibration phantom, preparing a third calibration phantom comprising a third plurality of slotted slabs arranged in the first vertical stack, the third calibration phantom prepared by removing or adding one or more slotted slabs to the first calibration phantom, and scanning the third calibration phantom.

20. The method of claim 16, wherein the calibration phantom holder comprises a base material used in the calibration operation.

* * * * *